US 7,076,297 B2

(12) United States Patent
Limousin et al.

(10) Patent No.: US 7,076,297 B2
(45) Date of Patent: Jul. 11, 2006

(54) ACTIVE IMPLANTABLE DEVICE MEDICAL SUCH AS PACEMAKER, DEFIBRILLATOR AND/OR CARDIOVERTOR OF THE AAI OR AAI/DDD TYPE

(75) Inventors: Marcel Limousin, Paris (FR); Amel Amblard, Conches-sur-Gondoire (FR)

(73) Assignee: ELA Medical S.A., Montrouge (FR)

( * ) Notice: Subject to any disclaimer, the term of this patent is extended or adjusted under 35 U.S.C. 154(b) by 118 days.

(21) Appl. No.: 10/830,967

(22) Filed: Apr. 23, 2004

(65) Prior Publication Data
US 2005/0240235 A1     Oct. 27, 2005

(51) Int. Cl.
*A61N 1/36* (2006.01)
(52) U.S. Cl. .................. 607/9; 607/4; 607/17
(58) Field of Classification Search ............. 607/4, 607/9, 14, 17, 25
See application file for complete search history.

(56) References Cited

U.S. PATENT DOCUMENTS

2001/0029392 A1   10/2001  Limousin .............. 607/5
2002/0095183 A1    7/2002  Casset et al. .......... 607/4
2002/0120301 A1*   8/2002  Levine et al. .......... 607/9
2004/0260349 A1*  12/2004  Stroebel .............. 607/9

\* cited by examiner

*Primary Examiner*—Robert E. Pezzuto
*Assistant Examiner*—Tammie K. Heller
(74) *Attorney, Agent, or Firm*—Orrick Herrington & Sutcliffe LLP

(57) ABSTRACT

An active implantable medical device, such as a pacemaker, defibrillator and/or cardiovertor having an AAI and/or an AAI/DDD operating mode. This device detects atrial and ventricular events and stimulates the atrium, and calculates an atrial escape interval (AEI). The device defines a critical period preceding or following the end of the AEI and determines, in the event of detection of a ventricular extrasystole (VES), if the moment of occurrence of the VES is in the critical period. The device then recognizes a risk of inappropriate operation and/or false diagnosis related to the temporal proximity of the VES and end of the AEI. In such a case, the device modifies an operating parameter so as to eliminate this risk, for example, by resetting the counting of AEI (AEI*) on detection of the VES. The device can also inhibit a switching of AAI mode to a DDD mode in the event of risk of false diagnosis of atrio-ventricular block.

31 Claims, 3 Drawing Sheets

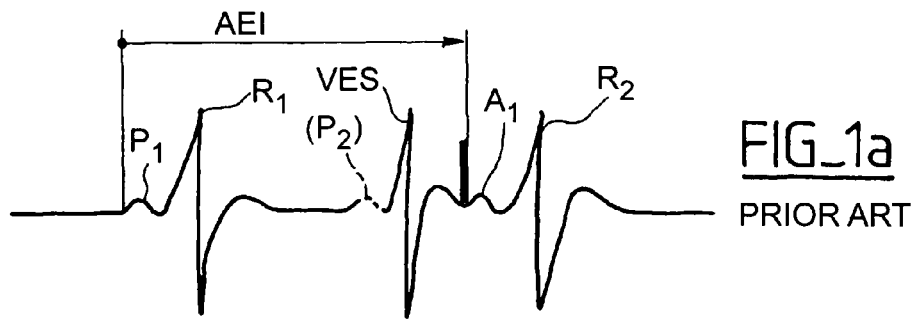
FIG_1a
PRIOR ART
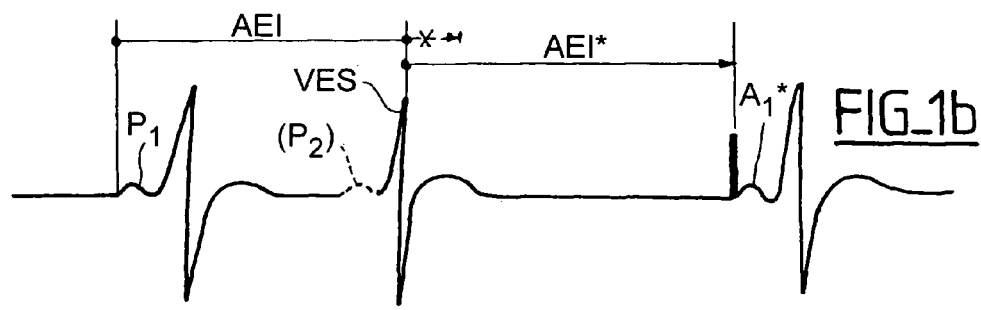
FIG_1b
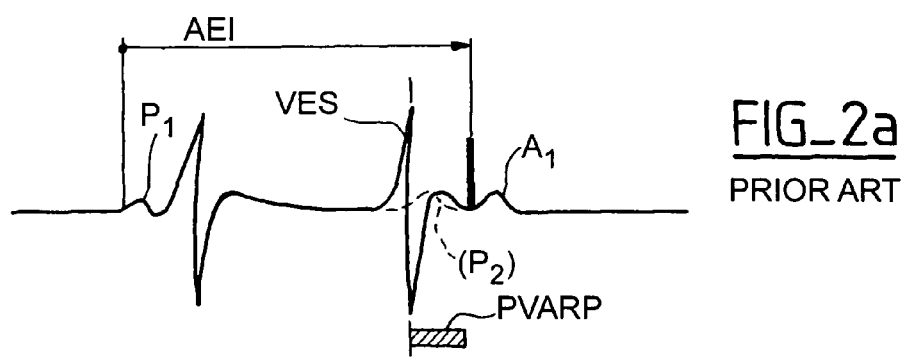
FIG_2a
PRIOR ART
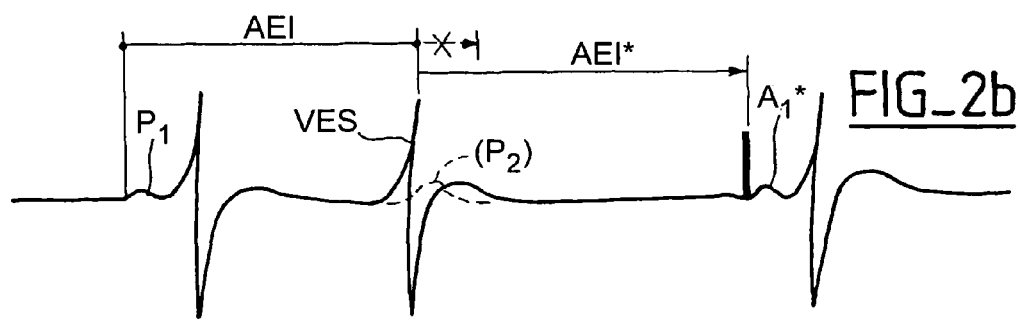
FIG_2b

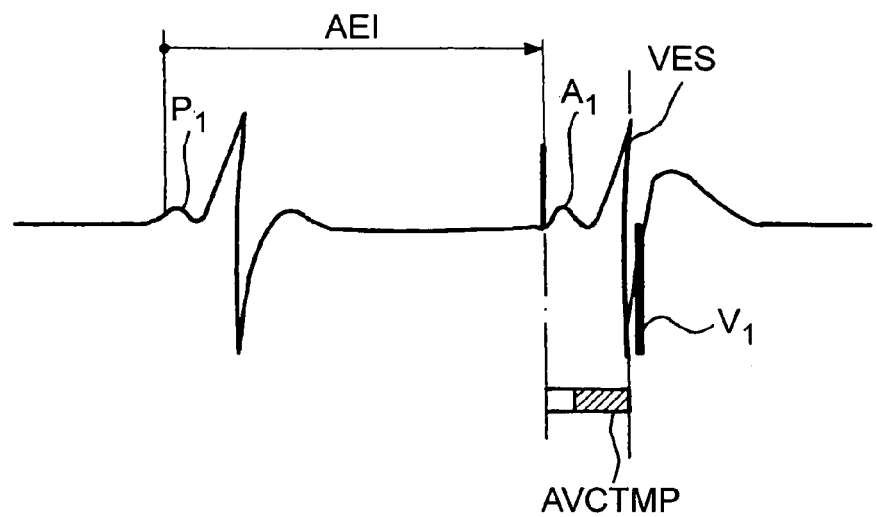
FIG_3
PRIOR ART
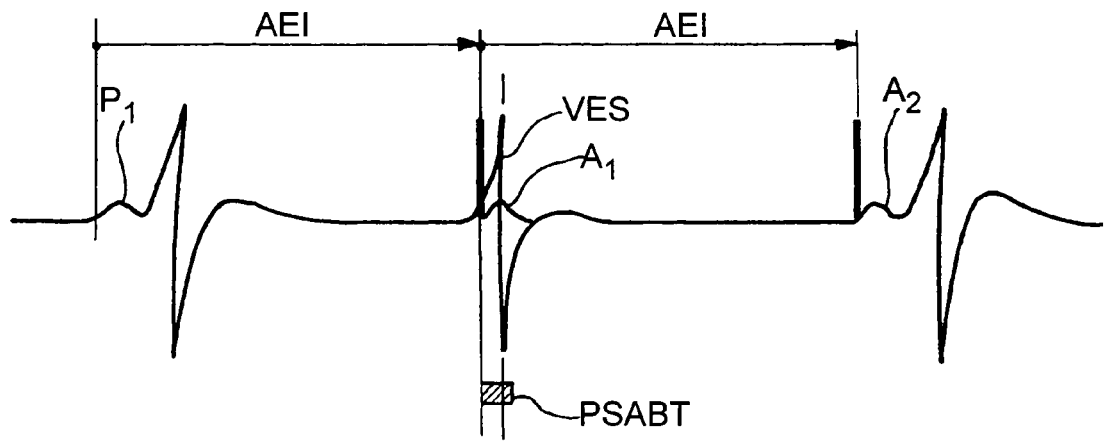
FIG_4
PRIOR ART

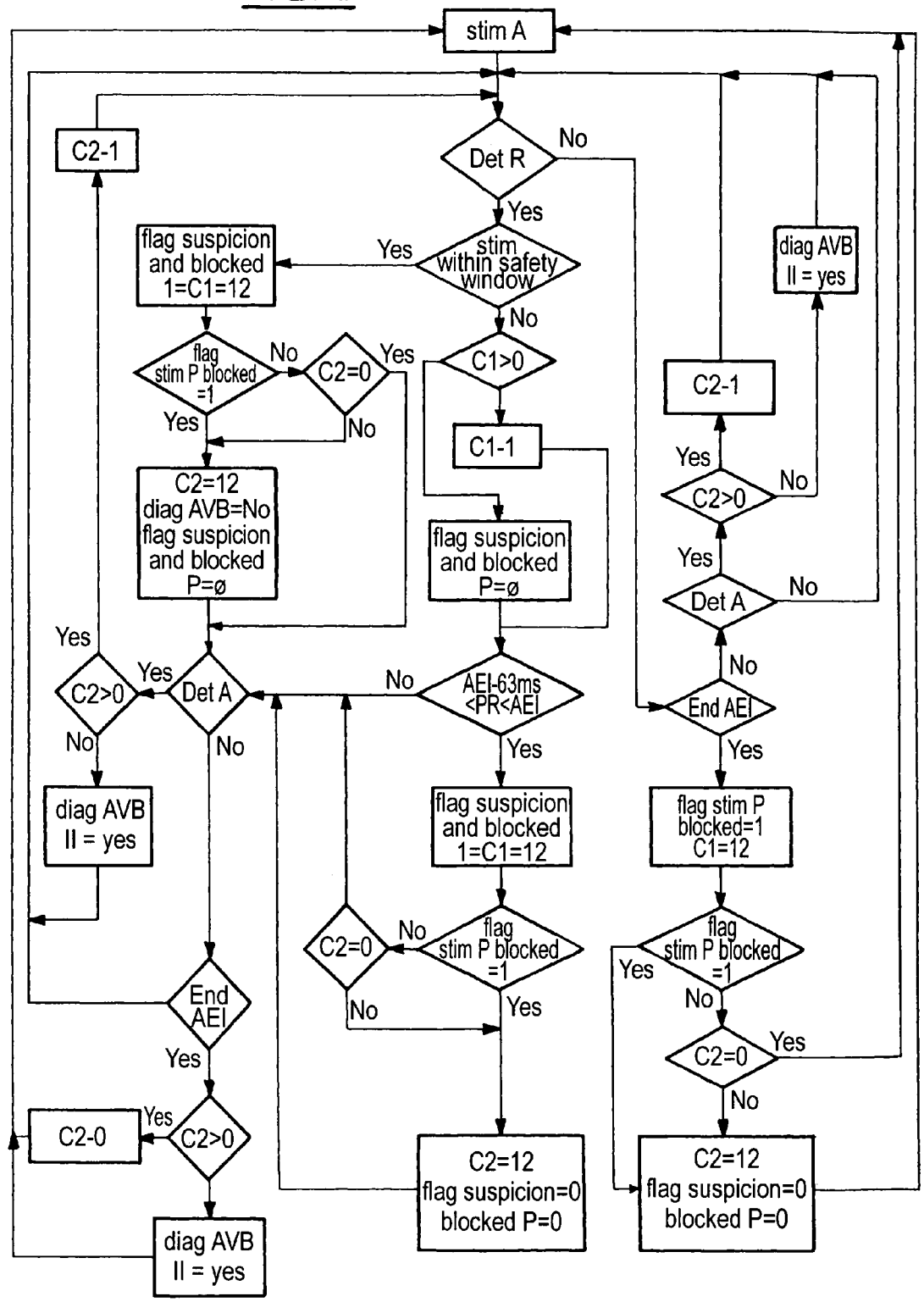
FIG_5

ACTIVE IMPLANTABLE DEVICE MEDICAL SUCH AS PACEMAKER, DEFIBRILLATOR AND/OR CARDIOVERTOR OF THE AAI OR AAI/DDD TYPE

FIELD OF THE INVENTION

The present invention relates to "active implantable medical devices" as defined by directive 90/385/CEE of Jun. 20, 1990 of the Council of the European Communities, more particularly to pacemaker devices, "multisite" devices (i.e., devices capable of pacing in three or four chambers of the heart), defibrillators and/or cardiovertors, making it possible to deliver to the heart pulses of low energy for the treatment of the disorders of the cardiac rhythm. It relates more particularly to those devices that include circuits for stimulation and circuits for detection on the atrium and the ventricle and can operate according to two pacing operating modes, DDD or AAI (the AAI mode being a DDD mode including a lengthened atrio-ventricular delay). Optionally, these devices can be equipped with a mode called "Automatic Mode Switching" ensuring an automatic switching between the DDD mode and the AAI mode based on satisfaction of predetermined criteria authorizing each mode switch.

However, as it would be appreciated by a person of ordinary skill in the art, the invention is not limited to devices with automatic mode switching, but can apply as well to devices configured for operating in the AAI mode alone, insofar as, in certain configurations, the invention proposes to modify the AAI operating mode, without having an automatic mode switching and/or for avoiding an automatic mode switching.

BACKGROUND OF THE INVENTION

The basic operating mode of a DDD/AAI cardiac pacemaker is an AAI mode, with a single chamber atrial stimulation and a monitoring (detection) of the ventricular activity. This mode is maintained as long as atrio-ventricular conduction is normal, i.e., as long as each atrial event (atrial detection, corresponding to a spontaneous activity, or atrial stimulation corresponding to a paced event) is followed by an associated ventricular detection. In certain circumstances there exist atrio-ventricular blocks (AVB) involving a temporary defect of the depolarization of the ventricle. In this case, the cardiac pacemaker switches automatically to operate in a DDD mode, with parameters optimized for a temporary AVB situation. After the disappearance of the AVB, and thus a re-establishment of spontaneous atrio-ventricular conduction, provided that a certain number of conditions are fulfilled, the cardiac pacemaker switches automatically to operate in the AAI mode. This automatic mode switching between DDD and AAI is described, for example, in EP-A-0 488 904 and its counterpart U.S. Pat. No. 5,318,594 commonly assigned herewith to ELA Médical, Montrouge, France.

The starting point of the present invention arises from certain observations made by the inventors at the time of a clinical follow-up of patients equipped with AAI or DDD/AAI devices that have automatic mode switching, when these patients presented ventricular extrasystoles (VES). VES are spontaneous ventricular events that are not preceded by an associated atrial depolarization and present a significant shortening of the ventricular interval RR (or VR) compared to the preceding ventricular event. According to the coupling of VES as compared to the preceding ventricular event, the VES can occur either simultaneously with the atrial depolarization of the following beat (i.e., the cardiac cycle), or at a moment close to the end of the atrial escape interval (AEI), i.e., at the moment when an atrial stimulation must be delivered in the absence of a spontaneous event detected in the atrium.

It was appreciated that, in a certain number of situations that will be described in more detail below, the known devices present limits in their capacity to detect or manage correctly the cardiac electric activity in the event that a VES has occurred at certain critical moments of the cardiac wave. This incapacity to manage correctly all situations that are likely to occur in the event of the occurrence of VES causes:

1. a delivery to the heart of inappropriate atrial or ventricular stimulations, that are therefore ineffective—and potentially disadvantagous—to the hemodynamic flow;
2. with these AAI/DDD devices having automatic mode switching, accidental switching to the DDD mode because of a false diagnosis of an atrio-ventricular block (the device believes that it has detected an AVB, whereas a spontaneous conduction is actually present); and
3. a combination of the above two erroneous actions, i.e., an inappropriate stimulation followed by an unnecessary switching to the DDD mode.

These inappropriate actions can create among certain vulnerable patients conditions that are favourable to the appearance of disorders of the ventricular rate/rhythm, which of course it is desirable to prevent.

OBJECTS AND SUMMARY OF THE INVENTION

To this end, the present invention is directed to an improved device and process in which an active implantable medical device, such as pacemaker, defibrillator and/or cardiovertor, includes:

means for detecting spontaneous atrial and ventricular events, including means for detecting an occurrence of ventricular extrasystoles among the spontaneous ventricular events, and means for atrial stimulation, including means for calculating an atrial escape interval and means for starting to count the calculated atrial escape interval on detection of an atrial event, and means for delivering an atrial stimulation at the end of the counted atrial escape interval if no spontaneous atrial event was detected in the interval.

According to the present invention, such a device also includes:

means for defining a critical period relative to the end of the counted atrial escape interval;

means for determining, in the event of a detection of a ventricular extrasystole, whether the moment of occurrence of the ventricular extrasystole is during said critical period;

means for recognizing an appearance of a risk condition, said risk condition based upon the temporal vicinity of the ventricular extrasystole and end of the atrial escape interval corresponding to an inappropriate operation and/or a false diagnosis, and means, responsive to determining that the ventricular extrasystole occurred in said critical period, for modifying at least one operating parameter of the device so as to eliminate the aforementioned risk condition.

The aforementioned critical period can proceed or follow the end of the counted atrial escape interval, and more preferably can be:

1. a period defined by a temporal window preceding the end of the atrial escape interval by a predetermined duration, for example, preceding the end of the atrial escape interval by less than about 63 ms;
2. a post-ventricular atrial refractory period (PVARP) following the end of the atrial escape interval, which count is started on detection of the ventricular extrasystole;
3. a period of monitoring atrio-ventricular cross-talk following the end of the atrial escape interval, which count is started on delivery of an atrial stimulation pulse at the end of the atrial escape interval; or
4. a period of post atrial stimulation blanking following the end of the atrial escape interval, which count is started on delivery of an atrial stimulation pulse at the end of the atrial escape interval.

For the first and second listed embodiments of critical period, the means for modifying at least one operating parameter of the device can in particular be a re-setting of the count of the atrial escape interval on detection of the ventricular extrasystolie (VES), (i.e., starting a new atrial escape interval). The invention in this aspect very advantageously applies to the above mentioned devices of the "Automatic Mode Switching" type, i.e., including, means for stimulating the ventricle; means for diagnosing an atrio-ventricular block; means for detecting the appearance and the repetition of spontaneous or stimulated atrial events not followed by detection of an associated spontaneous ventricular event; means for mode switching, able to control the switching from an AAI mode to a DDD mode in response to a proven diagnosis of an atrio-ventricular block, which device is characterized in that the aforementioned means for modifying at least one operating parameter includes means for inhibiting the aforementioned mode switching means from switching modes.

For the second and fourth listed embodiments of the critical period, the means for modifying at least one operating parameter of the device can then in particular, in response to an occurrence of a ventricular extrasystole, measure a lapse of time separating the last detected atrial event and the moment of occurrence of the ventricular extrasystole; set an indicator of suspicion of a false diagnosis if (i) the measured lapse of time is located inside an interval of a predetermined duration that is shorter than the duration of the calculated atrial escape interval, and/or (ii) a ventricular stimulation is delivered inside a safety window subsequent to the delivery of an atrial stimulation; detect and count atrial stimulations not followed by an associated spontaneous ventricular event; and inhibit the mode switching during a first predetermined number of cycles, for example, twelve cycles, in response to (a) detecting at least one atrial stimulation not followed by an associated spontaneous ventricular event, and/or (b) the indicator of suspicion of false diagnosis being in the set state. The aforementioned interval of predetermined time is, for example, an interval that is in the range of 10 to 120 ms, preferably 63 ms less than the duration of the atrial escape interval. The indication of suspicion is a parameter having a set state (e.g., a logical 1) corresponding to a suspicion existing, and a reset state (e.g., logical 0) in the absence of a suspicion. In this regard, the indicator of suspicion of false diagnosis can be reset (i.e., no suspicion exists) in response to detecting no atrial stimulation not followed by an associated spontaneous ventricular event during a second predetermined number of cycles, for example, twelve cycles.

For the second, third and fourth listed embodiments of critical period, the means for modifying at least one operating parameter of the device can in particular, in response to an occurrence of a ventricular extrasystole, measure a lapse of time separating the last detected atrial event and the moment of occurrence of the ventricular extrasystole; and prolong the atrial escape interval by a predetermined duration in response to (i) the measured lapse of time being located inside a predetermined time interval that is less than the duration of the calculated atrial escape interval, and/or (ii) a ventricular stimulation being delivered inside a safety window following the delivery of an atrial stimulation. The aforementioned predetermined duration of prolongation of the atrial escape interval is, for example, in the range of 10 to 120 ms, preferably 63 ms. The prolonged atrial escape interval can be restored to its initial value as calculated by the atrial stimulation means in response to detecting no atrial stimulation not followed by an associated spontaneous ventricular event during a predetermined number of cycles, for example, twelve cycles.

BRIEF DESCRIPTION OF THE DRAWINGS

Further benefits, features and characteristics of the present invention will become apparent to a person of ordinary skill in the art in view of the following detailed description of a preferred embodiment of the invention, made with reference to the annexed drawings, in which:

FIG. 1a illustrates a first case where the occurrence of a VES in a critical period induces an inappropriate operation, for a device of the prior art;

FIG. 1b illustrates the same situation as the FIG. 1a, in accordance with the present invention that makes it possible to avoid the inappropriate operation;

FIGS. 2a and 2b are homologous with FIGS. 1a and 1b, for a second case of occurrence of a VES in a critical period;

FIG. 3 illustrates a third case of occurrence of a VES in critical period, for a device of the prior art;

FIG. 4 illustrates a fourth case of occurrence of a VES in critical period, for a device of the prior art; and FIG. 5 is a flow chart illustrating an algorithm for the diagnosis of type II AVB, adapted according to the invention to suspend the treatment of this AVB II in the event of detection of a false positive resulting from the occurrence of a VES during a critical period.

DETAILED DESCRIPTION OF THE INVENTION

The invention can be implemented in any known manner of circuitry, and more preferably by suitable programming of the control software of known cardiac pacemakers of the double chamber type integrating a DDD mode and an AAI mode with monitoring of the ventricular activity. However, as indicated above, and as it hereafter will be seen, certain aspects the invention can also apply to the cardiac pacemaker functioning only in AAI mode, by adjustment of the conditions of implementation of this mode, as may be reflected in software instructions.

The following definitions are used in the continuation of the description.

Detection P or DetP; sensing of a spontaneous activity having its origin in the atrium; it will be considered that there is indeed a detection P if the detection is not followed in a given delay, for example, a 31 ms period, by a ventricular detection (if not, one would be in a situation of "ventricular far-field" i.e., sensing in the atrium a remote depolarization coming from the ventricle).

Detection R or DetR; sensing of a spontaneous activity having its origin in the ventricle.

Stimulation A or StimA; stimulation delivered to the atrium.

Stimulation V or StimV; stimulation delivered to the ventricle.

Atrial event; detection P or stimulation A.

Ventricular event; detection R or stimulation V.

Cardiac cycle; interval of time separating two events of comparable nature in the same cavity, for example, separating two detections P, or two stimulations A.

Average PP; average interval of the atrial rate, calculated, for example, over eight cardiac cycles not including an extrasystole.

Atrial escape interval (AEI); an interval of time, counted after a detection P or a stimulation A in the atrium, following which a stimulation A is delivered if no detection P is detected in the same cavity.

Ventricular extrasystolie (VES); a ventricular detection is a VES when it is preceded by a ventricular detection R or stimulation V, and when the ventricular event coupling interval (RR or VR) is less than or equal to a value, for example, 75% of the average RR.

For further details on the detection and the treatment of the extrasystoles, one will be able to refer to EP-A-0 550 342 and its counterpart U.S. Pat. No. 5,312,451 assigned to Ela Médical, which is incorporated herein by return in its entirety.

In the context of the present invention, the cardiac pacemaker is operating a conventional AAI mode with monitoring of the ventricular activity, i.e., an atrial detection outside of the refractory period (detection P) or an atrial stimulation (stimulation A) does not start an AVD, but rather starts an atrial escape interval AEI. For the AAI mode equipped with a monitoring of the ventricular activity, the algorithm in addition seeks the presence or the absence of a ventricular event, and in the presence of a ventricular event could give leave to suspect an AVB, so as, if required, to switch to the DDD mode of double chamber stimulation with atrioventricular association, i.e., with calculation and application of an AVD. Three situations can induce the switch to DDD mode:

1. A complete atrio-ventricular block, that is a condition manifested by "blocked" atrial waves (stimulated or spontaneous), i.e., atrial depolarizations that are not followed by ventricular depolarization. Typically, the mode switch intervenes in the event of a succession of two blocked waves, detected or stimulated, or if there are more than three seconds without a ventricular detection;
2. an atrio-ventricular block of second degree (AVB II), a condition which appears when the ratio of the number of non-extrasystolic P waves divided by the number of non extrasystolic R waves is greater than 1. The mode switching intervenes if, typically, the apparatus detects a ratio that is or greater than or equal to 12/9; and
3. an atrio-ventricular block of first degree (AVB I), a condition which is manifested by a delay of atrio-ventricular conduction that is greater than a given value, typically 350 ms after a spontaneous P-wave or 450 ms after a stimulated P-wave. The switching to the DDD mode intervenes after n consecutive cycles, where n is preferably 6.

In the presence of one of these criteria, the device automatically switches from AAI mode in DDD mode.

After a return of spontaneous ventricular activity over a certain number of cycles, or after a predetermined number of cycles in DDD mode, the device then automatically switches from DDD to AAI and remains in the AAI mode as long as none of the three above mentioned criteria for switching AAI to DDD is satisfied.

As the inventors have appreciated, the aforementioned clinical studies revealed several cases in which traditional operation in AAI mode and/or AAI/DDD automatic mode switching do not operate in an appropriate manner, because of the occurrence of a VES at a particular critical period of the cardiac rhythm.

The first case, illustrated in FIG. 1a, is that where an atrial detection $P_2$ (FIG. 1a) precedes by a little, typically less than 30 ms, an extrasystolic ventricular depolarization (VES). With a known device, atrial detection $P_2$ will be invalidated by the detection algorithm and cardiac rhythm analysis because the device is not able to discriminate between (1) a true spontaneous atrial depolarization, and (2) a situation of "far-field" ventricular detection in the atrium, i.e., an atrial detection which does not result from a depolarization of the atrium, but rather is a signal detected in the atrium coming from the detection of the VES "heard in the distance" after a delay. Being in doubt, the device considers that there was no P-wave and thus, in accordance with the operating AAI mode, does not recycle (i.e., restart the count) the AEI (the pure AAI mode being a mode without detection of ventricular activity). At the end of the escape interval AEI, as no spontaneous atrial detection was recognized and validated since following the $P_1$-wave, the cardiac pacemaker delivers an atrial stimulation inducing an atrial depolarization $A_1$. Compared to the preceding spontaneous atrial depolarization $P_2$ that was invalidated by the rate analysis algorithm, this stimulated atrial depolarization $A_1$ will be premature, and risks inducing a disorder of the atrial rate if it occurs during the time of vulnerability of the atrium.

Further, even if this stimulation induces an effective atrial depolarization, i.e., itself inducing a ventricular depolarization $R_2$ (FIG. 1a), the latter will be premature compared to the preceding ventricular event, i.e., the extrasystolic event VES. Such conditions are known to generate disorders of the ventricular rate/rhythm.

The solution suggested by the present invention, illustrated in FIG. 1b, concerns recycling the AEI on detection of a VES. The recycling of the AEI on this ventricular event will have the same effect as if it had been generated by a spontaneous atrial event. New interval AEI* will delay in time the delivery of the atrial stimulation pulse in the absence of spontaneous depolarization $A_1$* (FIG. 1b). Compared to the $P_2$ wave, the maximum error introduced by recycling the AEI on the ventricular event VES corresponds to the case when the spontaneous atrial event occurs at the end of the post-VES refractory period, which physiologically is acceptable (i.e., the maximum delay of stimulation is equal to the duration of the refractory period). Conversely, if the VES is strongly premature, recycling on this ventricular event will be without consequence, because the later atrial depolarization that will occur after the end of the post-VES refractory period will recycle the AEI again, corresponding to awaited behaviour in AAI mode.

The second case, illustrated in FIG. 2a, appears when an atrial depolarization $P_2$ intervenes either not before, but a little after the detection of the VES. In this case, atrial depolarization is not detected by the apparatus, because it occurs during the post-ventricular atrial refractory period (PVARP). This atrial depolarization $P_2$ not being taken into account, the AEI is not recycled and an atrial stimulation is thus delivered at the end of the AEI, inducing an undesirable atrial depolarization $A_1$. This atrial stimulation $A_1$ being more premature than the hidden atrial depolarization $P_2$, it can be ineffective, i.e., not induce a ventricular depolarization associated with conduction in the natural manner. The cardiac pacemaker thus detects a configuration with atrial stimulation not followed by ventricular depolarization, i.e., a situation of AVB. If this sequence repeats more than three times out of twelve, the device switches automatically to the DDD mode, in an inappropriate manner.

As may be appreciated, this second case is likely to present two disadvantages. One is the same hemodynamic flow problem as in the first case because of an atrial stimulation intervening at an inappropriate moment. The other is an error of diagnosis of AVB involving an inopportune mode switching if this diagnosis is repeated.

The solution in accordance with the present invention concerns, as in the first case, to recycle the AEI on detection of the VES, as illustrated on the FIG. 2b; the AEI is recycled as AEI*, causing a stimulation inducing an atrial depolarization $A_1$* respecting the natural rate of the patient (thus being satisfactory for the hemodynamic flow) and making it possible to induce in turn a ventricular depolarization (thus without detection of AVB) with a temporal error at the moment of delivery of this stimulation which remains within acceptable limits on the physiological level. The recycling of the AEI on the VES will have a second consequence, namely, that atrial stimulation $A_1$* no longer can be delivered prematurely after the VES and will depolarize the ventricle naturally by atrio-ventricular conduction, which are again excitable.

The third case, illustrated on FIG. 3, is when, in the absence of spontaneous atrial depolarization, a stimulation intervenes at the end of the escape interval AEI with application of a VES concomitant to the safety stimulation $V_1$ (see infra). The atrial stimulation $A_1$ at the end of the AEI delay will start a counting period known as an atrio-ventricular cross-talk monitoring period (AVCTMP), which is a window defined typically by an interval between 50 ms and 94 ms following the atrial stimulation $A_1$.

However, the device is unable to differentiate between a true ventricular depolarization (in this case the VES), and a detection in the ventricle of a signal that would come in fact from the atrial electric stimulus. Because of this uncertainty, by precaution, the device delivers a safety ventricular stimulation $V_1$, typically 100 ms after atrial stimulation $A_1$. This case does not induce a diagnosis of erroneous AVB; however, it is not a correct behaviour in the AAI mode, because an operation in AAI mode would normally not be influenced by the ventricular activity—which is not the case here, and thus there is a correlative disadvantage for the hemodynamic state.

The fourth case, illustrated in FIG. 4, is that where, as in the preceding case, the end of the AEI occurs a few milliseconds before the VES, with the VES occurring here during the post-stimulation atrial blanking time (PSABT). With the difference of the preceding case where the VES was detected but inoperative, here the VES is not even detected (the blanking interval temporarily blocking any detection of the signal after a stimulation, so as to avoid saturating the amplifier stages). The VES not being detected by the apparatus, the atrial stimulation $A_1$ started at the end of the AEI will not be able to induce ventricular depolarization, because the VES renders the tissues of conduction temporarily refractory. Consequently, the device considers that the $A_1$ wave is a blocked atrial wave and recycles a new interval AEI by indicating a diagnosis of AVB. This diagnosis is in fact a false positive, because the absence of conducted ventricular depolarization is due only to the fact that an intervening VES occurred, and not at the appearance of a conduction defect constitutive of a AVB.

As in the second above mentioned case, if this situation is repeated more than three times out of twelve, the device switches to the DDD mode, in an inappropriate manner because the switching is not the consequence of any real AVB. In addition to the recycling of the AEI on detection of the VES, which makes it possible to solve the problems involved in the first case and the second above mentioned case, the invention proposes two techniques applicable to solve the problems that have just been discussed related to the third case and the fourth case (and incidentally to the second case, as well).

The first technique, illustrated by the flow chart of FIG. 5, concerns, during a probable diagnosis of AVB II, to analyze the circumstances having led to the diagnosis of AVB so as to determine if it is a true AVB II or a false diagnosis due to a configuration corresponding to the one of the above mentioned cases and, if the latter to suspend the treatment of the AVB II by inhibition of any undesirable passage to the DDD mode. In addition to the abbreviations of the definitions indicated above (StimA, DetR, etc), one will indicate two particular counters C1 and C2 implemented by this flow chart. The counter C1 is a counter initialized, for example, at 12 (corresponding in this case to the numerator of the ratio 12/9 between the number of non-extrasystolic P waves and the number of non-extrasystolic R waves used for the diagnosis of AVB II as discussed above). The initialization of counter C2 is carried out during the detection of a suspect VES, occurring at the end of the AEI and corresponding to the above indicated case of a stimulation during the safety window, or in the case of a VES whose coupling interval is such that it occurs at the same time as the end of the AEI.

Counter C1 is decremented by one at each ventricular event associated with an atrial event or at each VES whose coupling interval presents a duration notably different from that of the AEI. When counter C1 reaches a zero value, this means that since twelve cycles of the ventricular events that have occurred are either depolarizations associated with a corresponding atrial event, or VES which do not occur at the end of the AEI; one can thus cancel the suspicion of AVB on VES occurring at the end of the AEI (hence resetting the suspicion indicator).

The counter C2, for example, is initialized to 12 (value given, for example, in the same way defined for counter C1), this initialization intervening when the algorithm detects either a stimulation in safety window, or a VES occurring at the end of the AEI, and that a blocked atrial stimulation was analyzed during the last twelve cycles. This counter C2 is decremented one on any ventricular event. In this way, when C2>0, the diagnosis of AVB II is inhibited. When C2 becomes equal to 0, then the diagnosis of AVB II is proven. More precisely, during detection of a VES, the device measures the interval between the last P-wave and the occurrence of the VES (interval [P, VES]). If this interval is close to the duration of the AEI, typically if: AEI−63 ms<[P, VES]<AEI, then an indicator of suspicion of false diagnosis is set to '1' (setting the "flag suspicion false diag" on the flow chart of FIG. 5). During a stimulation in the safety window, this indicator of suspicion is also set to '1'.

If the counter C2 of blocked atrial stimulations is equal to or greater than 1, and the indicator of suspicion of false diagnosis is also set to '1', then the diagnosis of AVB II is inhibited for a given length of time, for example, typically during twelve cycles. Thus, with three atrial stimulations blocked on twelve, one does not start a switching to the DDD mode—whereas with a traditional device one would cause such a switching.

If the device finds any VES of a duration close to the AEI (as discussed above) or no stimulation in the safety window, and no blocked atrial stimulation is detected during, for example, twelve cycles, then the indicator of suspicion of false diagnosis is reset to zero, just as the C2 counter is set to zero. On any detection of any of the three events described previously (i.e., of an event which causes the indicator of suspicion of false diagnosis to be set to '1'), then the counter C1 of inhibition of the AVB II diagnosis is re-initialized with the typical value, i.e., to 12 in the example given above. This causes the device to suspend switching to the DDD mode, the diagnosis of AVB II not having been proven.

A second technique concerns, during the detection of a VES close to the end to the AEI (in the meaning indicated above for the first technique), or at a stimulation in safety window, to prolong the atrial escape interval AEI, for example, by 63 ms duration. The prolongation of the escape interval makes it possible to avoid any conflict between a correct detection of the VES and a satisfactory behaviour in AAI mode. This prolongation will continue during a given delay, for example, during twelve cycles, unless one of the two events above is not again detected by the device.

Suitable devices for which the present invention has application include, for example, the Talent™, Symphony™, and Rhapsody™, brand pacemakers and Alto™ brand of defibrillators, all available from Ela Médical, Montrouge France. These devices are microprocessor based systems with memory, data registers and the like (microcontrollers) having circuits for receiving, conditioning and processing detected electrical signals, and are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricular, in the left and/or right chambers, as well as any stimulation circuits for delivering low energy stimulation pulses for treatment of disorders of the cardiac rates, are well known and any suitable design may be used.

One skilled in the art will appreciate that the present invention can be practiced by other than the described embodiments, which are presented for purposes of illustration and not of limitation.

We claim:

1. An active implantable medical device comprising:
   means for detecting spontaneous atrial and ventricular events, including means for detecting an occurrence of ventricular extrasystoles among detected spontaneous ventricular events,
   means for stimulating the atrium, including means for calculating an atrial escape interval, means for starting to count said calculated atrial escape interval on detection of an atrial event, and means for delivering an atrial stimulation at the end of the counted atrial escape interval if no spontaneous atrial event is detected in said atrial escape interval,
   means for defining a critical period relative to the end of the calculated atrial escape interval,
   means for determining, in response to a detected ventricular extrasystole, whether the detected ventricular extrasystole is during said critical period, means for recognizing a risk condition of inappropriate operation and/or false diagnosis of the device based upon the temporal proximity of the detected ventricular extrasystole to the end of the atrial escape interval, and
   means, responsive to a recognized risk condition, for modifying an operating parameter of the device so as to eliminate said recognized risk condition.

2. The device of claim 1, wherein said critical period further comprises a temporal window preceding the end of the atrial escape interval by a predetermined duration.

3. The device of claim 2 wherein said means for modifying at least one operating parameter further surprises means for resetting the counting of the atrial escape interval in response to a detected ventricular extrasystole.

4. The device of claim 1, wherein said critical period further comprises a temporal window preceding the end of the atrial escape interval by less than 63 ms.

5. The device of claim 1, in wherein said critical period is a post-ventricular atrial refractory period following the end of the atrial escape interval, that begins counting on detection of a ventricular extrasystole.

6. The device of claim 5 wherein said means for modifying at least one operating parameter further comprises means for resetting the counting of the atrial escape interval in response to a detected ventricular extrasystole.

7. The device of claim 5 wherein said means for modifying said at least one operating parameter further comprises means, responsive to a detected ventricular extrasystole, for measuring a lapse of time separating the last detected atrial event and the moment of occurrence of the detected ventricular extrasystole, means for setting an indicator of suspicion of false diagnosis in response to (i) the measured lapse of time being located inside a predetermined time interval, less than the calculated atrial escape interval, and/or (ii) a detected ventricular stimulation occurring inside a safety window subsequent to a delivery of an atrial stimulation, means for detecting and counting atrial stimulations not followed by an associated spontaneous ventricular event, and means for inhibiting the mode switching means during a first predetermined number of cycles in response to (i) detecting at least one atrial stimulation not followed by an associated spontaneous ventricular event, and (ii) the indicator of suspicion of false diagnosis bring in a set state.

8. The device of claim 7, wherein said predetermined time interval comprises an interval that is shorter than the duration of the atrial escape interval by no more than 63 ms.

9. The device of claim 7, wherein said first predetermined number of cycles is twelve cycles.

10. The device of claim 10, wherein said means for modifying said at least one operating parameter further comprises means for resetting said indicator of suspicion of false diagnosis in response to detecting an atrial stimulation not followed by an associated spontaneous ventricular event during a second predetermined number of cycles.

11. The device of claim 10, wherein said second predetermined number is twelve cycles.

12. The device of claim 5 wherein the means for modifying said at least one operating parameter further comprises;

means responsive to a detected ventricular extrasystole for measuring a lapse of time separating the last detected atrial event and the moment of occurrence of the detected ventricular extrasystole, and means for prolonging the atrial escape interval by a predetermined duration in response to (i) the measured lapse of time being located inside a predetermined time interval of less than the duration of the calculated atrial escape, and/or (ii) a ventricular stimulation being delivered inside a safety window subsequent to the delivery of an atrial stimulation.

13. The device of the claim 12, wherein said predetermined duration for prolonging the atrial escape interval is 63 ms.

14. The device of claim 12, wherein said means for modifying said at least one operating parameter comprises means for restoring the prolonged atrial escape interval to the calculated atrial escape interval in response to detecting no atrial stimulation not followed by an associated spontaneous ventricular event during a predetermined number of cycles.

15. The device of claim 14, in which the wherein said predetermined number of cycles is twelve cycles.

16. The device of claim 1, wherein said critical period further comprises an atrio-ventricular cross-talk monitoring period following the end of the atrial escape interval that begins counting on an atrial stimulation at the end of the atrial escape interval.

17. The device of claim 16, wherein the means for modifying said at least one operating parameter further comprises;

means responsive to a detected ventricular extrasystole, for measuring a lapse of time separating the last detected atrial event and the moment of occurrence of the detected ventricular extrasystole, and means for prolonging the atrial escape interval by a predetermined duration in response to (i) the measured lapse of time being located inside a predetermined time interval of less than the duration of the calculated atrial escape, and/or (ii) a ventricular stimulation being delivered inside a safety window subsequent to the delivery of an atrial stimulation.

18. The device of the claim 17, wherein said predetermined duration for prolonging the atrial escape interval is 63 ms.

19. The device of claim 17, wherein said means for modifying said at least one operating parameter comprises means for restoring the prolonged atrial escape interval to the calculated atrial escape interval in response to detecting no atrial stimulation not followed by an associated spontaneous ventricular event during a predetermined number of cycles.

20. The device of claim 19, in which the wherein said predetermined number of cycles is twelve cycles.

21. The device of the claim 1, wherein said critical period further comprises a post-stimulation atrial blanking period following the end of the atrial escape interval that begins counting on an atrial stimulation at the end of the atrial escape interval.

22. The device of claim 21, wherein the means for modifying said at least one operating parameter further comprises;

means responsive to a detected ventricular extrasystole, for measuring a lapse of time separating the last detected atrial event and the moment of occurrence of the detected ventricular extrasystole, and means for prolonging the atrial escape interval by a predetermined duration in response to (i) the measured lapse of time being located inside a predetermined time interval of less than the duration of the calculated atrial escape, and/or (ii) a ventricular stimulation being delivered inside a safety window subsequent to the delivery of an atrial stimulation.

23. The device of the claim 22, wherein said predetermined duration for prolonging the atrial escape interval is 63 ms.

24. The device of claim 22, wherein said means for modifying said at least one operating parameter comprises means for restoring the prolonged atrial escape interval to the calculated atrial escape interval in response to detecting no atrial stimulation not followed by an associated spontaneous ventricular event during a predetermined number of cycles.

25. The device of claim 24, in which the wherein said predetermined number of cycles is twelve cycles.

26. The device of claim 21 wherein said means for modifying said at least one operating parameter further comprises means, responsive to a detected ventricular extrasystole, for measuring a lapse of time separating the last detected atrial event and the moment of occurrence of the detected ventricular extrasystole.

27. The device of claim 26, wherein said predetermined time interval comprises an interval that is shorter than the duration of the atrial escape interval by no more than 63 ms.

28. The device of claim 26, wherein said first predetermined number of cycles is twelve cycles.

29. The device claim 26, wherein said means for modifying said at least one operating parameter further comprises, means for resetting said indicator of suspicion of false diagnosis in response to detecting an atrial stimulation not followed by an associated spontaneous ventricular event during a second predetermined number of cycles.

30. The device of claim 29, wherein said second predetermined number of cycles is twelve cycles.

31. The device of claim 1, further comprising;

means for stimulating the ventricle, means for detecting an appearance and repetition of spontaneous or stimulated atrial events not followed by detection of an associated spontaneous ventricular event, and diagnosing an atrio-ventricular block, mode switching means, able to control the switching from a AAI mode to a DDD mode response a diagnosis of an atrio-ventricular block, wherein said means for modifying said at least one operating parameter of the device further comprises means for inhibiting said mode switching means from switching from AAI to DDD mode.

* * * * *